US008410177B2

(12) United States Patent
Namboothiri et al.

(10) Patent No.: US 8,410,177 B2
(45) Date of Patent: Apr. 2, 2013

(54) CURCUMIN DERIVATIVES

(75) Inventors: Irishi N. N. Namboothiri, Mumbai (IN);
Narasimham Ayyagari, Mumbai (IN);
Deena Jose, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 329 days.

(21) Appl. No.: 12/717,774

(22) Filed: Mar. 4, 2010

(65) Prior Publication Data

US 2011/0160276 A1 Jun. 30, 2011

(30) Foreign Application Priority Data

Dec. 30, 2009 (IN) .......................... 3024/MUM/2009

(51) Int. Cl.
*A61K 31/12* (2006.01)
(52) U.S. Cl. ........ 514/678; 514/679; 514/706; 514/740; 514/579; 568/8; 568/308
(58) Field of Classification Search .................. 514/675, 514/678, 679, 579; 568/8, 308
See application file for complete search history.

(56) References Cited

U.S. PATENT DOCUMENTS

| | | | |
|---|---|---|---|
| 4,350,705 | A | 9/1982 | Hamano et al. |
| 4,522,811 | A | 6/1985 | Eppstein et al. |
| 6,906,105 | B2 | 6/2005 | Bowen et al. |
| 7,371,766 | B2 | 5/2008 | Snyder et al. |
| 2003/0092772 | A1 | 5/2003 | Reksohadiprodjo et al. |
| 2004/0167217 | A1 | 8/2004 | Scapagnini et al. |
| 2006/0275283 | A1 | 12/2006 | Van Vlijmen et al. |
| 2006/0276536 | A1 | 12/2006 | Vander Jagt et al. |
| 2007/0060644 | A1* | 3/2007 | Vander Jagt et al. ......... 514/475 |
| 2007/0141183 | A1 | 6/2007 | Babish et al. |
| 2007/0270464 | A1 | 11/2007 | Liotta et al. |

OTHER PUBLICATIONS

Hoashi et al., Tetrahedron, 2006, 62, pp. 365-374.*
Anand, P. et al., "Bioavailability of Curcumin: Problems and Promises," *Molecular Pharmaceutics*, 2007, vol. 4, No. 6, pp. 807-818; published by American Chemical Society.
Shi, W. et al., "Synthesis of Monofunctional Curcumin Derivatives, Clicked Curcumin Dimer, and a PAMAM Dendrimer Curcumin Conjugate for Therapeutic Applications," *Organic Letters*, 2007, vol. 9. No. 26, pp. 5461-5464; published by American Chemical Society.
Aggarwal, B. B. et al., "Molecular targets of dietary agents for prevention and therapy of cancer," *Biochemical Pharmacology*, 2006, vol. 71, pp. 1397-1421; published by Elsevier Inc.
Goel, A. et al., "Curcumin as "Curecumin": From kitchen to clinic," *Biochemical Pharmacology*, 2008, vol. 75, pp. 787-809; published by Elsevier Inc.
Lachman, E., "Curcumin: A Look into the Occurrence, Bioactivity, Biosynthesis, and Synthesis of the Turmeric Extract," *Chemistry*, Fall 2008, vol. 150, 4 pages.

Aggarwal, B. B. et al., "Anticancer Potential of Curcumin: Preclinical and Clinical Studies," *Anticancer Research*, 2003, vol. 23, pp. 363-398.
Selvam, C. et al., "Design, synthesis, biological evaluation and molecular docking of curcumin analogues as antioxidant, cyclooxygenase inhibitory and anti-inflammatory agents," *Bioorganic & Medicinal Chemistry Letters*, 2005, vol. 15, pp. 1793-1797; published by Elsevier Ltd.
Nurfina, A. N. et al., "Synthesis of some symmetrical curcumin derivatives and their antiinflammatory activity," *Eur. J. Med. Chem.*, 1997, vol. 32, pp. 321-328; published by Elsevier, Paris.
Weber, W. M. et al., "Activation of NFkB is inhibited by curcumin and related enones," *Bioorganic & Medicinal Chemistry*, 2006, vol. 14, pp. 2450-2461; published by Elsevier Ltd.
Weber, W. M. et al., "Anti-oxidant activities of curcumin and related enones," *Bioorganic & Medicinal Chemistry*, 2005, vol. 13, pp. 3811-3820; published by Elsevier Ltd.
Nichols, C. E. et al., "Microwave-assisted synthesis of curcumin analogs," *ARKIVOC*, 2006, (xiii), pp. 64-72.
Li, L. et al., "Liposome-Encapsulated Curcumin: In Vitro and In Vitro Effects on Proliferation, Apoptosis, Signaling, and Angiogenesis," *Cancer*, Sep. 15, 2005; vol. 104, No. 6, pp. 1322-1331; published online Aug. 9, 2005 in Wiley InterScience.
Menon, L. G. et al., "Anti-metastatic activity of curcumin and catechin," *Cancer Letters*, 1999, vol. 141, pp. 159-165; published by Elsevier Science Ireland Ltd.
Litwinienko, G. et al., "Abnormal Solvent Effects on Hydrogen Atom Abstraction. 2. Resolution of the Curcumin Antioxidant Controversy. The Role of Sequential Proton Loss Electron Transfer," *J. Org. Chem.*, 2004, vol. 69, pp. 5888-5896; published by American Chemical Society.

(Continued)

*Primary Examiner* — Sreeni Padmanabhan
*Assistant Examiner* — Shobha Kantamneni
(74) *Attorney, Agent, or Firm* — Foley & Lardner LLP

(57) ABSTRACT

A compound has Formula VIII where, X is —C(O)R, —C(O)OR, —CN, —NO$_2$, —S(O)$_2$R', —P(O)(OR)$_2$; each R is individually H, alkyl, or alkenyl; R' is alkyl or akenyl; R$^1$ is aryl, alkenyl, arylalkenyl, heterocyclyl, or heteroaryl; and R$^2$, R$^3$, R$^4$, R$^5$, R$^6$, R$^7$, R$^8$, R$^9$, R$^{10}$, and R$^{11}$ are individually H, alkoxy, or hydroxy. In some cases, X is NO$_2$.

Formula VIII

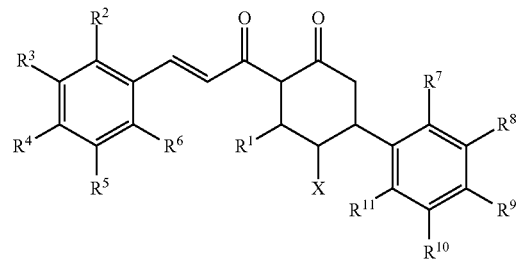

Pharmaceutical compositions of the compound of Formula VIII with a pharmaceutically acceptable carrier may be prepared. The compounds may be used for inhibition of cyclooxygenase-2.

10 Claims, No Drawings

OTHER PUBLICATIONS

Yang, F. et al., Curcumin Inhibits Formation of Amyloid β Oligomers and Fibrils, Binds Plaques, and Reduces Amyloid in Vivo, *The Journal of Biological Chemistry*, Feb. 18, 2005, vol. 280, No. 7, pp. 5892-5901.

Mazumder, A. et al., "Curcumin Analogs with Altered Potencies against HIV-1 Integrase as Probes for Biochemical Mechanisms of Drug Action," *J. Med. Chem.*, 1997, vol. 40, No. 19, pp. 3057-3063; published by American Chemical Society.

Bisht, S. et al., "Polymeric nanoparticle-encapsulated curcumin ("nanocurcumin"): a novel strategy for human cancer therapy," *J. Nanobiotechnology*, Apr. 17, 2007, vol. 5, No. 3, 18 pages.

Kurien, B. T. et al., "Increasing aqueous solubility of curcumin for improving bioavailability," *Trends in Pharmacological Sciences*, 2009, vol. 30, No. 7, pp. 334-335; published by Elsevier Ltd.

Ohori, H. et al., "Synthesis and biological analysis of new curcumin analogues bearing an enhanced potential for the medicinal treatment of cancer," *Mol. Cancer Ther.*, Oct. 2006, vol. 5, No. 10, pp. 2563-2571.

Mishra, S. et al., "Synthesis and exploration of novel curcumin analogues as anti-malarial agents," *Bioorganic & Medicinal Chemistry*, 2008, vol. 16, pp. 2894-2902; published by Elsevier Ltd.

Song, Y.-M. et al., "Syntheses, characterization and biological activities of rare earth metal complexes with curcumin and 1,10-phenanthroline-5,6-dione," *Journal of Inorganic Biochemistry*, 2009, vol. 103, pp. 396-400; published by Elsevier Inc.

Mosley, C. A. et al., "Highly active anticancer curcumin analogues," *Adv. Exp. Med. Biol.*, 2007, vol. 595, pp. 77-103.

Chattopadhyay, I. et al., "Turmeric and curcumin: Biological actions and medicinal applications," *Current Science*, Jul. 10, 2004, vol. 87, No. 1, pp. 44-53.

Shoba, G. et al., "Influence of Piperine on the Pharmacokinetics of Curcumin in Animals and Human Volunteers," *Planta Med.*, May 1998, vol. 64, pp. 353-356.

Pabon, H. J. J., "A Synthesis of Curcumin and Related Compounds," *Recueil*, 1964, vol. 83, pp. 379-386.

Sharma, O. P., "Antioxidant activity of curcumin and related compounds," *Biochemical Pharmacology*, May 1976, vol. 25, No. 9, pp. 1811-1812; published by Pergamon Press.

International Search Report for PCT/IB2010/001337 mailed Sep. 29, 2010.

Papadakis, P. E. et al., "Acylation of 5-(p-acetoxyphenyl)-4,6-dicarbethoxycyclohexanedione-1,3," *J. Am. Chem. Soc.*, 1953, vol. 75, pp. 5436-5437.

International Preliminary Report on Patentability for Intl. Pat. Appln. No. PCT/IB2010/001337, issued on Jul. 4, 2012, 4 pp.

Written Opinion of the International Searching Authority for Intl. Pat. Appln. No. PCT/IB/2010/001337, mailed on Sep. 29, 2010, 3 pp.

* cited by examiner

CURCUMIN DERIVATIVES

CROSS-REFERENCE TO RELATED APPLICATION

This application claims priority to India Patent Application No. 3024/MUM/2009, filed Dec. 30, 2009, the entire contents of which are incorporated by reference herein and for all purposes as if fully set forth herein.

TECHNOLOGY

This technology is generally related to derivatives of curcumin.

BACKGROUND

Curcumin (1; diferuloylmethane; 1,7-bis-(4-hydroxy-3-methoxyphenyl)-1,6-heptadiene-3,5-dione) is a yellow pigment and an active ingredient in turmeric (*Curcuma Longa*). Turmeric contains curcumin along with other curcuminoids such as demethoxycurcumin and bis-demethoxycurcumin.

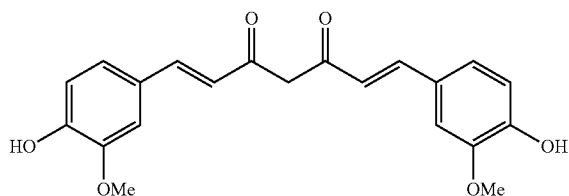

1

The yellow color of turmeric is due to the presence of the highly conjugated bis-phenolic β-diketone moiety in curcumin. The β-diketone moiety exists in equilibrium between keto and enol forms, as shown for example in Scheme 1. The energy of the enol form is 6.85 kcal/mol lower than that of the β-diketone form of Curcumin 1, suggesting that the enol form of curcumin predominates in solution.

SUMMARY

In one aspect, a compound of Formula VIII is provided:

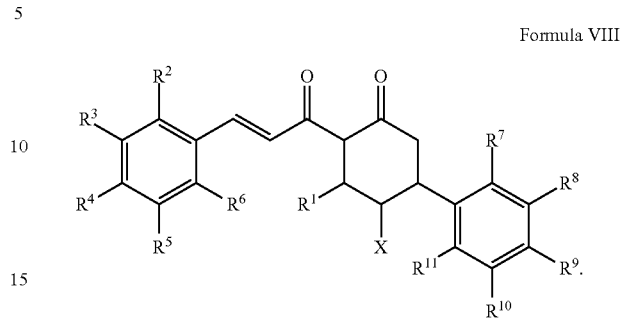

Formula VIII

According to some embodiments, X is —C(O)R, —C(O)OR, —CN, —NO$_2$, —S(O)$_2$R', —P(O)(OR)$_2$; each R is individually H, alkyl, or alkenyl; R' is alkyl or akenyl; $R^1$ is aryl, alkenyl, arylalkenyl, heterocyclyl, or heteroaryl; and $R^2$, $R^3$, $R^4$, $R^5$, $R^6$, $R^7$, $R^8$, $R^9$, $R^{10}$ and $R^{11}$ are individually H, alkoxy, or hydroxy. In some embodiments, at least two of $R^2$, $R^3$, $R^4$, $R^5$, $R^6$, $R^7$, $R^8$, $R^9$, $R^{10}$, and $R^{11}$ are alkoxy. In some embodiments, $R^1$ is phenyl, alkenyl, thiophenyl, or furyl. In some embodiments, $R^4$ and $R^9$ are alkoxy. In some embodiments, $R^4$ and $R^9$ are methoxy or ethoxy. In some embodiments, $R^2$, $R^3$, $R^6$, $R^7$, $R^{10}$, and $R^{11}$ are H. In some embodiments, $R^1$ is p-methoxyphenyl, 3,4-dimethoxyphenyl, phenyl, p-chlorophenyl, thiophen-2-yl, benzo[d]-1,3-dioxozolyl, furan-2-yl, 3-nitrophenyl, or 2-phenylethenyl.

In some embodiments, X is NO$_2$. In some embodiments, $R^1$ is phenyl, alkenyl, thiophenyl, or furyl. In some such embodiments, $R^4$ and $R^9$ are alkoxy. In some such embodiments, $R^4$ and $R^9$ are methoxy or ethoxy. In some such embodiments, $R^2$, $R^3$, $R^6$, $R^7$, $R^{10}$, and $R^{11}$ are H. In some such embodiments, $R^1$ is p-methoxyphenyl, 3,4-dimethoxyphenyl, phenyl, p-chlorophenyl, thiophen-2-yl, benzo[d]-1,3-dioxozolyl, furan-2-yl, 3-nitrophenyl, or 2-phenylethenyl.

In some embodiments, Formula VIII is 3,5-bis(4-methoxyphenyl)-2-((E)-3-(4-methoxyphenyl)acryloyl)-4-nitrocyclohexanone; 3-(3,4-dimethoxyphenyl)-5-(4-methoxyphenyl)-2-((E)-3-(4-methoxyphenyl)acryloyl)-4-nitrocyclohexanone; 5-(4-methoxyphenyl)-2-((E)-3-(4-methoxyphenyl)acryloyl)-4-nitro-3-phenylcyclohexanone; 3-(4-chlorophenyl)-5-(4-methoxyphenyl)-2-((E)-3-(4-meth- Scheme 1

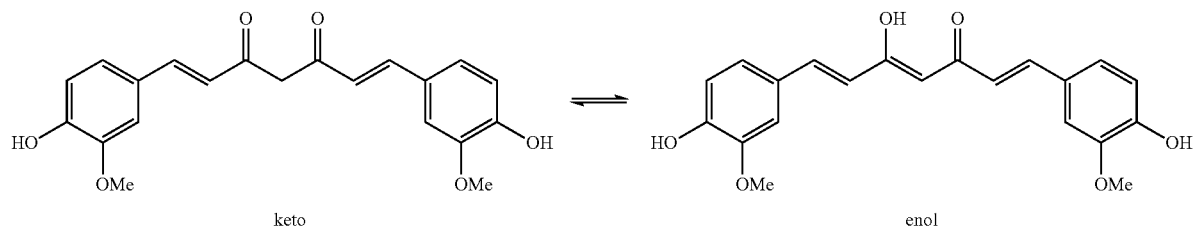

keto  enol

Despite a broad range of biological activity of curcumin, its low solubility in aqueous solvent and concomitant poor bioavailability hamper its use for pharmaceutical applications.

oxyphenyl)acryloyl)-4-nitrocyclohexanone; 5-(4-methoxyphenyl)-2-((E)-3-(4-methoxyphenyl)acryloyl)-4-nitro-3-(thiophen-2-yl)cyclohexanone; 3-(benzo[a][1,3]dioxol-5- yl)-5-(4-methoxyphenyl)-2-((E)-3-(4-methoxyphenyl) acryloyl)-4-nitrocyclohexanone; 3-(furan-2-yl)-5-(4-methoxyphenyl)-2-((E)-3-(4-methoxyphenyl)acryloyl)-4-nitrocyclohexanone; 5-(4-methoxyphenyl)-2-((E)-3-(4-methoxyphenyl)acryloyl)-4-nitro-3-(3-nitrophenyl) cyclohexanone; 5-(4-methoxyphenyl)-2-((E)-3-(4-methoxyphenyl)acryloyl)-4-nitro-3-styrylcyclohexanone; 5-(3,4-dimethoxyphenyl)-3-(4-methoxyphenyl)-2-((E)-3-(3,4-dimethoxyphenyl)acryloyl)-4-nitrocyclohexanone; 5-(4-hydroxy-3-methoxyphenyl)-2-((E)-3-(4-hydroxy-3-methoxyphenyl)acryloyl)-3-(4-methoxyphenyl)-4-nitrocyclohexanone; or 3-(4-methoxyphenyl)-4-nitro-5-phenyl-2-((E)-3-phenylacryloyl)cyclohexanone.

In another aspect, a method of preparing a compound of Formula VIII is provided, including reacting a compound of Formula VI with a nitroalkene in the presence of a base, where:

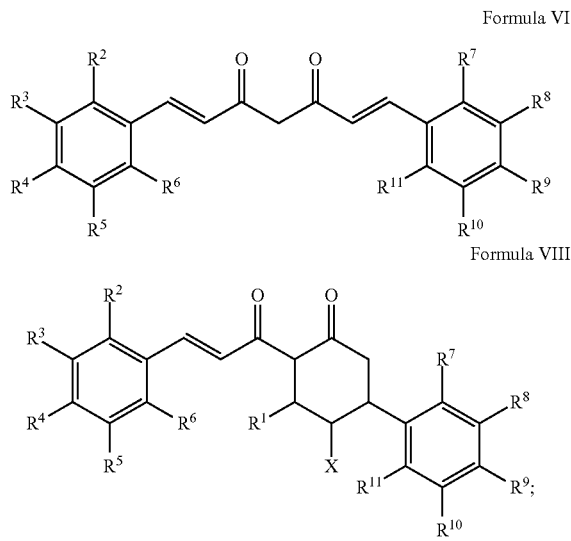

the nitroalkene has formula $R^1CH=CHNO_2$; $R^1$ is aryl, alkene, heterocyclyl, or heteroaryl; and $R^2$, $R^3$, $R^4$, $R^5$, $R^6$, $R^7$, $R^8$, $R^9$, $R^{10}$, and $R^{11}$ are individually H, alkoxy, or hydroxy. In some embodiments, the base is a metal alkoxide, metal hydroxide, metal carbonate, metal oxide, metal amide, an amine, a hindered amine, or a mixture of any two or more thereof. In some such embodiments, the base is 1,4-diazabicyclo[2.2.2]octane, diaza(1,3)bicyclo[5.4.0]undecane, $K_2CO_3$, $KOBu^t$, $K_2O$, KOH, $Na_2CO_3$, $NaOBu^t$, $Na_2O$, NaOH, $Li_2CO_3$, $LiOBu^t$, $Li_2O$, LiOH, $KNMe_2$, $NaNMe_2$, $LiNMe_2$, $KNEt_2$, $NaNEt_2$, $LiNEt_2$, KOMe, KOEt, $KOPr^n$, $KOPr^i$, NaOMe, NaOEt, $NaOPr^n$, $NaOPr^i$, LiOMe, LiOEt, $LiOPr^n$, $LiOPr^i$, piperidine, pyridine, 4-dimethylaminopyridine, 2,6-dimethylpyridine, 2,6-dimethyl-4-methylpyridine, 2,6-di-tert-butylpyridine, 2,6-di-tert-butyl-4-methylpyridine, or a mixture of any two or more thereof.

In some embodiments of the method, the reacting is conducted in a solvent. In some such embodiments, the solvent is acetonitrile, tetrahydrofuran, methylene chloride, chloroform, water, or a mixture of any two or more thereof. In some embodiments, the solvent is acetonitrile-water or tetrahydrofuran-water.

In another aspect, a pharmaceutical composition is provided including the compound of Formula VIII, and a pharmaceutically acceptable carrier.

In another aspect, a method is provided for inhibiting cyclooxygenase-2 in a subject. The method includes administering the pharmaceutical composition including the compound of Formula VIII, and a pharmaceutically acceptable carrier.

In another aspect, a method is provided for inhibiting transcription factor NFκB in a subject. The method includes administering the pharmaceutical composition including the compound of Formula VIII, and a pharmaceutically acceptable carrier.

In another aspect, a method is provided for inhibiting CD13/aminopeptidase N in a subject. The method includes administering the pharmaceutical composition including the compound of Formula VIII, and a pharmaceutically acceptable carrier.

In another aspect, a method is provided including administering a pharmaceutical composition including the compound of Formula VIII, and a pharmaceutically acceptable carrier to a subject in need of an anti-oxidant.

In another aspect, a method is provided for treating an inflammation disorder resulting from a condition in a subject comprising administering the pharmaceutical composition including the compound of Formula VIII, and a pharmaceutically acceptable carrier to the subject. In some embodiments, the inflammation disorder is asthma; lung inflammation; tuberculosis; leprosy; sarcoidosis; and silicosis; nephritis; arthritis; amyloidosis; rheumatoid arthritis; ankylosing spondylitis; chronic bronchitis; scleroderma; lupus; polymyositis; appendicitis; inflammatory bowel disease; ulcers; Sjorgen's syndrome; Reiter's syndrome; psoriasis; pelvic inflammatory disease; orbital inflammatory disease; thrombotic disease; inappropriate allergic responses to poison ivy, pollen, and insect stings; allergic responses to foods; atopic dermatitis; or contact dermatitis

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. The present technology is also illustrated by the examples herein, which should not be construed as limiting in any way.

Curcumins are an important class of biologically active molecules, and it is useful to exploit them as substrates for the synthesis of various mimics. Curcumins are utilized herein as Michael donors with various acceptors such as but not limited to azodicarboxylates, nitroalkenes, α,β-unsaturated aldehydes, enones, nitroso compounds, imines etc. Stereoselective Michael addition of curcumin with various acceptors is valuable for the synthesis of its mimics and analogues.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In general, "substituted" refers to an alkyl or alkenyl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Unless expressly indicated otherwise, alkyl groups may be substituted, or unsubstituted.

The terms "cyclic alkyl" or "cycloalkyl" refers to a saturated or partially saturated non-aromatic cyclic alkyl groups of from 3 to 14 carbon atoms and no ring heteroatoms and having a single ring or multiple rings including fused and bridged ring systems. Unless expressly indicated otherwise, cycloalkyl groups may be substituted or unsubstituted. Cycloalkyl or cyclic alkyl groups include mono-, bi- or tricyclic alkyl groups having from 3 to 14 carbon atoms in the ring(s), or, in some embodiments, 3 to 12, 3 to 10, 3 to 8, or 3 to 4, 5, 6 or 7 carbon atoms. Exemplary monocyclic cycloalkyl groups include, but not limited to, cyclopropyl, cyclobutyl, cyclopentyl, cyclohexyl, cycloheptyl, and cyclooctyl groups. Bi- and tricyclic ring systems include both bridged cycloalkyl groups and fused rings, such as, but not limited to, bicyclo[2.1.1]hexane, adamantyl, decalinyl, and the like.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Aryl group includes both substituted and unsubstituted aryl groups. Substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms.

Heterocyclyl groups includes non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. Unless expressly indicated otherwise, heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl(azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Unless expressly indicated otherwise, heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl(pyrrolopyridyl), indazolyl, benzimidazolyl, imidazopyridyl(azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

In one aspect, curcumin derivatives are provided. For example, in some embodiments, the curcumin derivatives include those such as a compound of Formula VIII:

Formula VIII

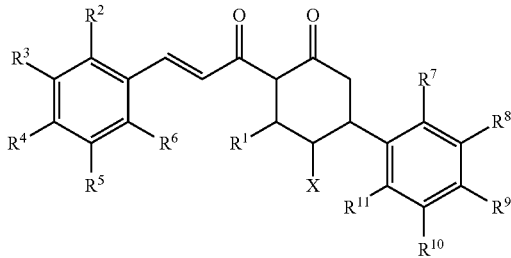

In Formula VIII, X is —C(O)R, —C(O)OR, —CN, —NO$_2$, —S(O)$_2$R', —P(O)(OR)$_2$; each R is individually H, alkyl, aryl, or alkenyl; R' is alkyl, aryl or akenyl; $R^1$ is aryl, alkenyl, arylalkenyl, heterocyclyl, or heteroaryl; and $R^2$, $R^3$, $R^4$, $R^5$, $R^6$, $R^7$, $R^8$, $R^9$, $R^{10}$, and $R^{11}$ are individually H, alkoxy, or hydroxy. In some embodiments, at least two of $R^2$, $R^3$, $R^4$, $R^5$, $R^6$, $R^7$, $R^8$, $R^9$, $R^{10}$, and $R^{11}$ are alkoxy.

Curcumin derivatives contain at least four stereocenters, all of which are located on the cyclohexanone ring. While it is possible to prepare each of the stereoisomers of the curcumin derivatives, through selection of appropriate stereospecific starting materials, or stereospecific or asymmetric catalysts, the methods described below are stereospecific to the compound of Formula VIII*. It is worth noting, that because the keto and enol forms are in tautomeric equilibrium, the stereochemistry at the undefined bond may be fluxional as well. As indicated in Formula VIII*, the olefinic bond is in a trans (i.e. "E") configuration.

Formula VIII*

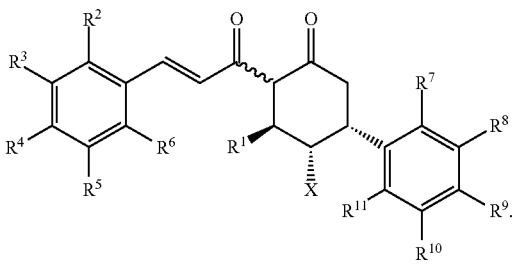

In some embodiments of Formula VIII, $R^1$ is phenyl, alkenyl, thiophenyl, or furyl. In some embodiments, X is NO$_2$. In such embodiments, the compound of Formula VIII is prepared from a curcumin derivative by reaction with a nitroalkene of Formula $R^1$—CH=CHNO$_2$. In some embodiments, $R^4$ and $R^9$ are alkoxy.

In some embodiments, $R^4$ and $R^9$ are methoxy or ethoxy. In some embodiments, $R^2$, $R^3$, $R^6$, $R^7$, $R^{10}$, and $R^{11}$ are H. In some other embodiments, $R^8$ is H. In such embodiments, the compound of Formula VIII may have the structure of the compound of Formula IX:

Formula IX

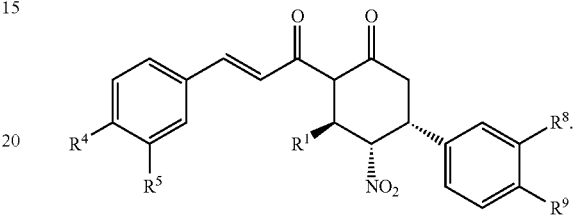

In other embodiments, in the compounds of Formula VIII and IX, $R^1$ is p-methoxyphenyl, 3,4-dimethoxyphenyl, phenyl, p-chlorophenyl, thiophen-2-yl, benzo[d]-1,3-dioxozolyl, furan-2-yl, 3-nitrophenyl, or 2-phenylethenyl. In other embodiments, in the compounds of Formula VIII and IX, $R^1$ is phenyl, alkenyl, thiophenyl, or furyl. In other embodiments, in the compounds of Formula VIII and IX, $R^4$ and $R^9$ are alkoxy. In other embodiments, in the compounds of Formula VIII and IX, $R^4$ and $R^9$ are methoxy or ethoxy.

In some specific embodiments, the compound of Formula VIII is 3,5-bis(4-methoxyphenyl)-2-((E)-3-(4-methoxyphenyl)acryloyl)-4-nitrocyclohexanone; dimethoxyphenyl)-5-(4-methoxyphenyl)-2-((E)-3-(4-methoxyphenyl)acryloyl)-4-nitrocyclohexanone; 5-(4-methoxyphenyl)-2-((E)-3-(4-methoxyphenyl)acryloyl)-4-nitro-3-phenylcyclohexanone; 3-(4-chlorophenyl)-5-(4-methoxyphenyl)-2-((E)-3-(4-methoxyphenyl)acryloyl)-4-nitrocyclohexanone; 5-(4-methoxyphenyl)-2-((E)-3-(4-methoxyphenyl)acryloyl)-4-nitro-3-(thiophen-2-yl)cyclohexanone; 3-(benzo[a][1,3]dioxol-5-yl)-5-(4-methoxyphenyl)-2-((E)-3-(4-methoxyphenyl)acryloyl)-4-nitrocyclohexanone; 3-(furan-2-yl)-5-(4-methoxyphenyl)-2-((E)-3-(4-methoxyphenyl)acryloyl)-4-nitrocyclohexanone; 5-(4-methoxyphenyl)-2-((E)-3-(4-methoxyphenyl)acryloyl)-4-nitro-3-(3-nitrophenyl)cyclohexanone; 5-(4-methoxyphenyl)-2-((E)-3-(4-methoxyphenyl)acryloyl)-4-nitro-3-styrylcyclohexanone; 5-(3,4-dimethoxyphenyl)-3-(4-methoxyphenyl)-2-((E)-3-(3,4-dimethoxyphenyl)acryloyl)-4-nitrocyclohexanone; 5-(4-hydroxy-3-methoxyphenyl)-2-((E)-3-(4-hydroxy-3-methoxyphenyl)acryloyl)-3-(4-methoxyphenyl)-4-nitrocyclohexanone; or 3-(4-methoxyphenyl)-4-nitro-5-phenyl-2-((E)-3-phenylacryloyl)cyclohexanone.

The synthesis of curcumin, and substituted curcumins, involves the reaction between an aromatic aldehyde, with acetyl acetone, and is illustrated in Scheme 2. Thus, the aromatic aldehyde controls which curcumin analog is prepared, as illustrated. $R^{2-11}$ in Scheme 2 are as defined above. Boric anhydride is then used to provide the boron bis(acetylacetonate) complex (α) in which the nucleophilicity of active methylene group is masked by complex formation. Normal aldol condensation with the terminal methyl groups of this complex, followed by the cleavage of this complex by dilute mineral acid, results in the compound of Formula VI.

Scheme 2:

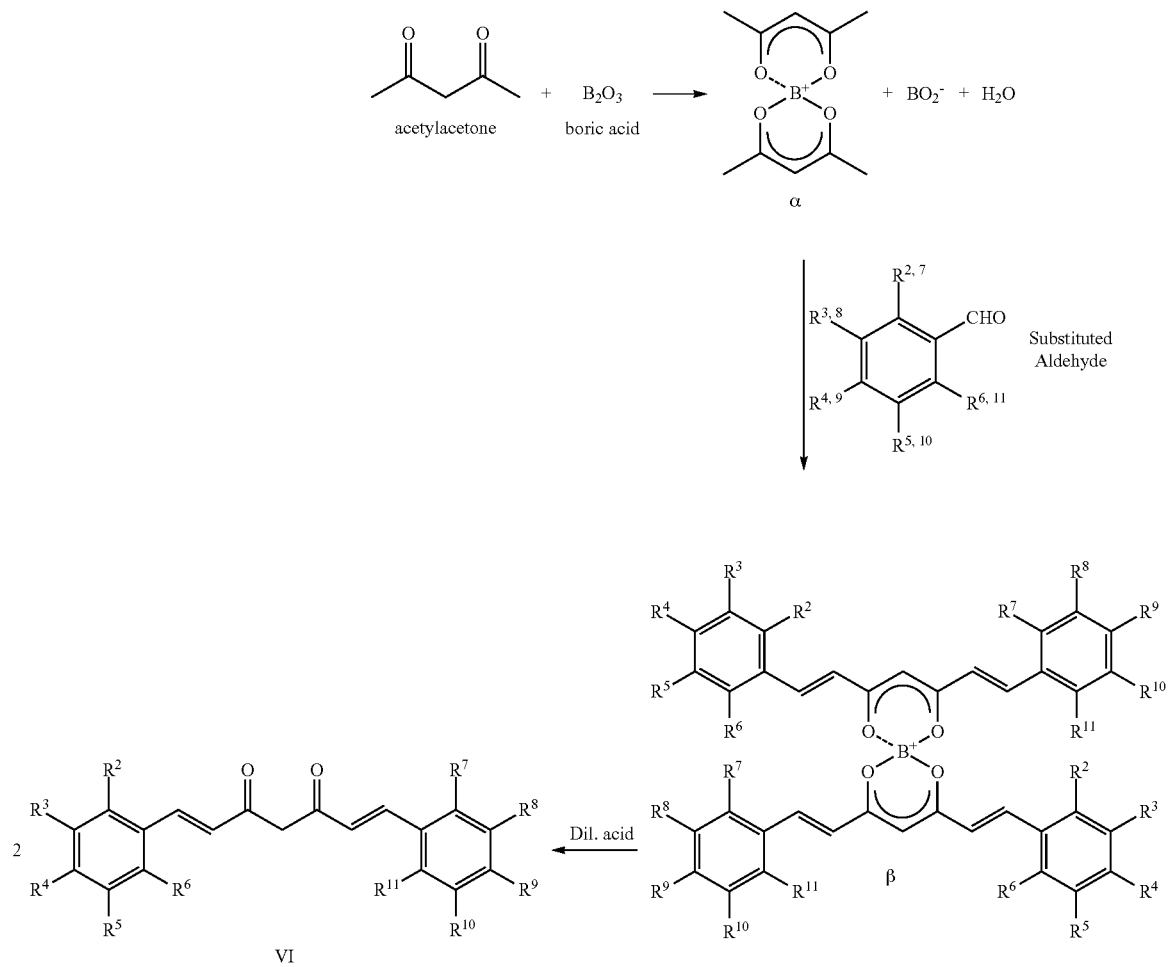

According to another aspect a method of preparing compounds of Formula VIII are provided. The method proceeds through a double Michael addition. The method includes reacting a compound of Formula VI with a nitroalkene in the presence of a base, as illustrated in Scheme 3.

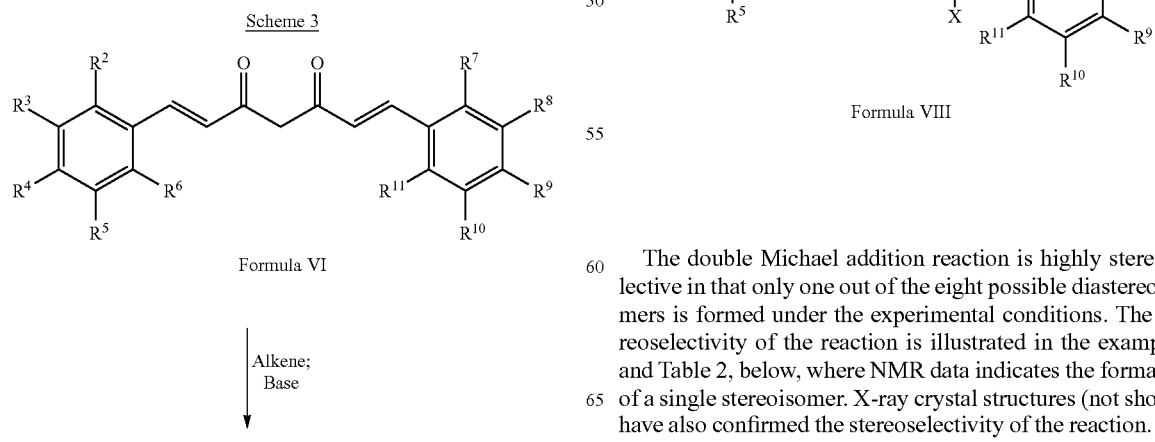

The double Michael addition reaction is highly stereoselective in that only one out of the eight possible diastereoisomers is formed under the experimental conditions. The stereoselectivity of the reaction is illustrated in the examples, and Table 2, below, where NMR data indicates the formation of a single stereoisomer. X-ray crystal structures (not shown) have also confirmed the stereoselectivity of the reaction. The compound formed has Formula VIII*:

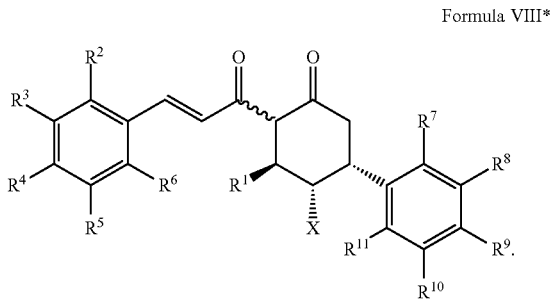

Formula VIII*

In one embodiment, the alkene that is used in the reaction of Scheme 3 is a nitroalkene of formula $R^1CH=CHNO_2$, where $R^1$ is H, alkyl, aryl, alkene, heterocyclyl, or heteroaryl. In some such embodiments, the nitroalkene is a β-aryl nitroethene, heteroaryl nitroethene, styrenyl nitroethene, β-alkyl nitroethene, α,β-disubstituted nitroethene. In other embodiments, the alkene is a Michael acceptor alkene such as an enal, enone, acrylate, acrylonitrile, vinylsulfone, vinyl phosphonate, and the like. Where $R^2$, $R^3$, $R^4$, $R^5$, $R^6$, $R^7$, $R^8$, $R^9$, $R^{10}$, and $R^{11}$ are defined as above. In some embodiments, the compounds of Formula VI and VIII in Scheme 3, are represented by the compounds of Formula VII and IX, respectively:

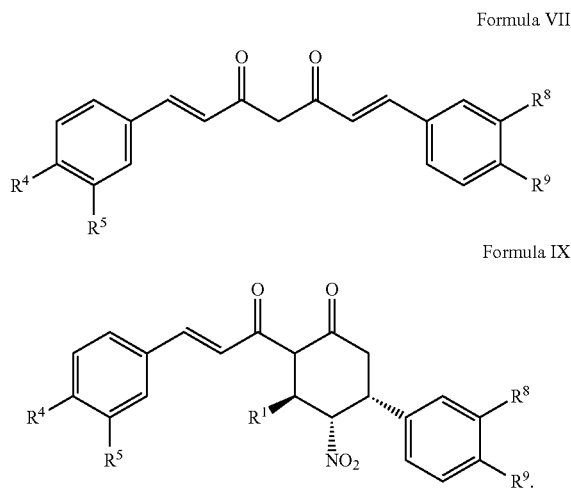

Formula VII

Formula IX

The base used in the method may include those such as a metal alkoxide, metal hydroxide, metal carbonate, metal oxide, metal amide, an amine, a hindered amine, or a mixture of any two or more such bases. Examples of bases include, but are not limited to 1,4-diazabicyclo[2.2.2]octane, diaza(1,3)bicyclo[5.4.0]undecane, $K_2CO_3$, $KOBu^t$, $K_2O$, KOH, $Na_2CO_3$, $NaOBu^t$, $Na_2O$, NaOH, $Li_2CO_3$, $LiOBu^t$, $Li_2O$, LiOH, $KNMe_2$, $NaNMe_2$, $LiNMe_2$, $KNEt_2$, $NaNEt_2$, $LiNEt_2$, KOMe, KOEt, $KOPr^n$, $KOPr^i$, NaOMe, NaOEt, $NaOPr^n$, $NaOPr^i$, LiOMe, LiOEt, $LiOPr^n$, $LiOPr^i$, piperidine, pyridine, 4-dimethylaminopyridine, 2,6-dimethylpyridine, 2,6-dimethyl-4-methylpyridine, 2,6-di-tert-butylpyridine, 2,6-di-tert-butyl-4-methylpyridine, or a mixture of any two or more such compounds. In some embodiments, the base is $K_2CO_3$. While the amount of base to be used may be determined experimentally and optimizing for yield, in some embodiments, the amount of base used is about 2 equivalents based upon the amount of the compound of Formula VI that is used.

As described below, the reaction is conducted in a solvent. Suitable solvents include, but are not limited to, acetonitrile, tetrahydrofuran, methylene chloride, chloroform, water, or a mixture of any two or more such solvents. In some embodiments, the solvent is a solvent mixture such as, but not limited to acetonitrile-water or tetrahydrofuran-water. In some embodiments, the ratio of solvent to water is about 1.5:0.2. In some embodiments, where the solvent is tetrahydrofuran-water, the ratio is about 1.5:0.2.

In some embodiments, an asymmetric catalyst is used in the method of preparation. In some embodiments, the catalyst is an amino acid or an alkaloid. For example, the catalyst may be proline or cinchonine, or a thiourea derivative thereof.

In some embodiments, the reactions are carried out at elevated, room, or low temperatures. For example, the reaction may be carried out in refluxing solvent, at room temperature, or chilled by an ice bath. Such temperatures can drive the reaction forward, prevent side reactions, or moderate the reaction process. In some embodiments, the reaction is carried out at about room temperature (i.e. about 298K).

The compounds of Formula VIII and IX may be used in pharmaceutical compositions for treating a variety of conditions or disease states in a subject. As such, in some embodiments, a pharmaceutical composition is provided including the compound of Formula VIII, and a pharmaceutically acceptable carrier. In other embodiments, a pharmaceutical composition is provided including the compound of Formula VIII, and a pharmaceutically acceptable carrier.

As used herein, the pharmaceutically acceptable carrier includes any and all solvents, dispersion media, coatings, antibacterial and antifungal agents, isotonic agents, absorption delaying agents, and the like. The use of such media and agents for pharmaceutically active substances is well known in the art. The complex or compound may be administered to an individual in an appropriate diluent or adjuvant, or in an appropriate carrier such as human serum albumin or liposomes. Supplementary active compounds can also be used with the complex. Pharmaceutically acceptable diluents include saline and aqueous buffer solutions. Adjuvants contemplated herein include resorcinols, non-ionic surfactants such as polyoxyethylene oleyl ether and hexadecyl polyethylene ether. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, Pa. 18$^{th}$ ed. (1990)). The pharmaceutical compositions are generally formulated as sterile, substantially isotonic and in full compliance with all Good Manufacturing Practice (GMP) regulations of the U.S. Food and Drug Administration.

The term "pharmaceutically-acceptable," and grammatical variations thereof, refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. A person of ordinary skill in the art, would have no difficulty determining the appropriate timing, sequence and dosages of administration for particular drugs and compositions.

Preferred examples of such carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the compounds, use thereof in the compositions is contemplated. Supplementary active compounds can also be incorporated into the compositions.

A pharmaceutical composition is formulated to be compatible with its intended route of administration. The compounds can be administered by parenteral, topical, intravenous, oral, subcutaneous, intraarterial, intradermal, transdermal, rectal, intracranial, intraperitoneal, intranasal; intramuscular route or as inhalants. The compounds can optionally be administered in combination with other agents that are at least partly effective in treating various diseases including inflammatory diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the compounds in the required amount in an appropriate solvent with one or a combination of ingredients enumerated above, as required. Generally, dispersions are prepared by incorporating the compounds into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The compounds can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the compounds can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The compounds can also be prepared as pharmaceutical compositions in the form of suppositories (e.g., with conventional suppository bases such as cocoa butter and other glycerides) or retention enemas for rectal delivery.

In one embodiment, the compounds are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

Alternatively, the compounds of Formula VIII and IX may find use in the preparation of a medicament that is useful in treating a variety of conditions or disease states in a subject. As used herein, "treating" or "treatment" of a disease state or condition in a patient refers to (1) preventing the disease or condition from occurring in a patient that is predisposed or does not yet display symptoms of the disease; (2) inhibiting the disease or condition or arresting its development; or (3) ameliorating or causing regression of the disease or condition. As used herein, "subject" refers to mammals, and may include humans and/or non-human mammals.

The compounds of Formula VIII and IX may be used in an effective amount as anti-inflammatory agents that act by inhibiting up-regulation of cyclooxygenase-2 (COX-2). Thus, in some embodiments, a method is provided for treating an inflammatory disorder resulting from a condition in a subject comprising administering the pharmaceutical composition including the compound of Formula VIII or IX, and a pharmaceutically acceptable carrier to the subject. In some embodiments, the inflammation disorder is asthma; lung inflammation; tuberculosis; leprosy; sarcoidosis; and silicosis; nephritis; arthritis; amyloidosis; rheumatoid arthritis; ankylosing spondylitis; chronic bronchitis; scleroderma; lupus; polymyositis; appendicitis; inflammatory bowel disease; ulcers; Sjorgen's syndrome; Reiter's syndrome; psoriasis; pelvic inflammatory disease; orbital inflammatory disease; thrombotic disease; inappropriate allergic responses to poison ivy, pollen, and insect stings; allergic responses to foods; atopic dermatitis; or contact dermatitis The compounds of Formula VIII and IX may be used in an effective amount as anti-oxidants. The main characteristic of an anti-oxidant is the ability to trap free radicals that are present in biological systems.

The compounds of Formula VIII and IX may be used in an effective amount to treat cancer in a subject through anti-metastatic activity or anti-angiogenesis activity. Although not wishing to be limited by any particular theory, anti-metastatic activity may be due to the ability of the compound to induce apoptosis by inhibiting the transcription factor NFκB. Anti-angiogenesis activity may be due to the inhibition of CD13/aminopeptidase N.

As used herein, the term "effective amount" of a compound is a quantity sufficient to achieve a desired therapeutic and/or prophylactic effect, for example, an amount which results in the prevention of or a decrease in the symptoms associated with a disease that is being treated. The amount of compound administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compounds of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. The compounds can also be administered in combination with each other, or with one or more additional therapeutic compounds.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology, thus generally described, will be understood more readily by reference to the following examples, which are provided by way of illustration and are not intended to be limiting in any way.

EXAMPLES

The present technology is further illustrated by the following examples, which should not be construed as limiting in any way.

Example 1

General synthesis. The synthesis of curcumin and its analogues, involves the reaction between vanillin, or other aromatic aldehydes, with acetyl acetone (10), and is illustrated in Scheme 4, below. Thus, the aromatic aldehyde controls which curcumin analog is prepared. Boric anhydride (11) is then used to provide the boron bis(acetylacetonate) complex (12) in which the nucleophilicity of active methylene group is masked by complex formation. Normal aldol condensation with the terminal methyl groups of this complex followed by the cleavage of this complex by dilute mineral acid results in curcumin (15).

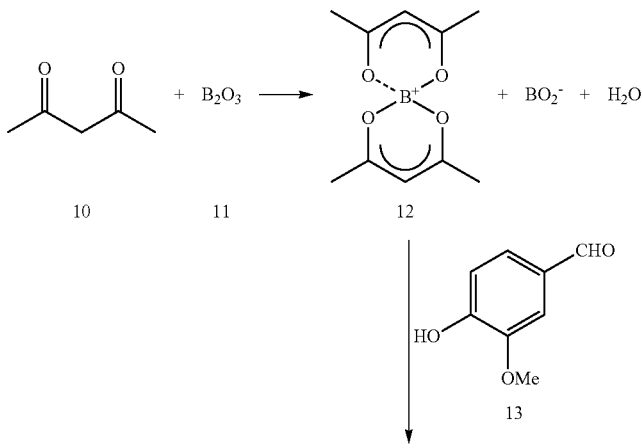

Scheme 4

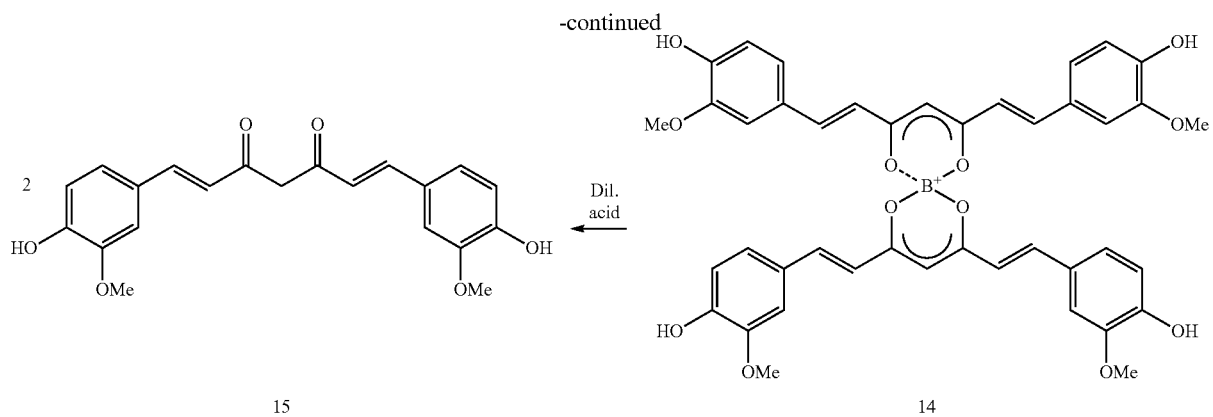

The double, Michael addition of curcumin 20 to nitroalkene 21 may be carried out in the presence of different bases (1 equiv) in various solvents, at room temperature. A product 22 is obtained by the double Michael addition reaction of Scheme 5.

Scheme 5

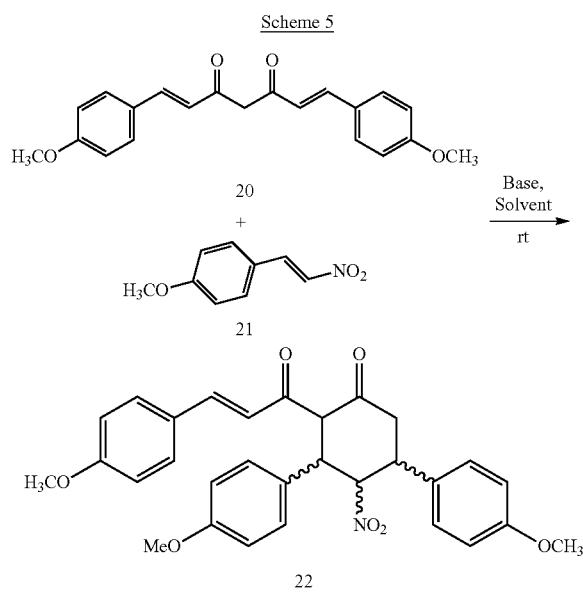

Example 2

Screening of solvents and bases for the synthesis of compound 22. An initial screening was carried out to optimize the reaction conditions for the synthesis of 22 as shown in Table 1.

TABLE 1

Base and Solvent Conditions for Curcumin Synthesis

| Entry | Base[b] | Solvent | Yield (%)[d] |
|---|---|---|---|
| 1 | DABCO | $CH_3CN$ | —[e] |
| 2 | DBU | $CH_3CN$ | 30 |
| 3 | $K_2CO_3$ | $CH_3CN$ | 40 |
| 4 | $^tBuOK$ | THF | 53 |
| 5 | $K_2CO_3$[c] | $CH_3CN$ | —[f] |

TABLE 1-continued

Base and Solvent Conditions for Curcumin Synthesis

| Entry | Base[b] | Solvent | Yield (%)[d] |
|---|---|---|---|
| 6 | $K_2CO_3$ | $CH_2Cl_2$ | —[e] |
| 7 | $K_2CO_3$ | $CHCl_3$ | —[e] |
| 8 | $K_2CO_3$ | $CH_2Cl_2$ (1.5 mL):$H_2O$ (0.2 mL) | —[e] |
| 9 | $K_2CO_3$ | $CHCl_3$ (1.5 mL):$H_2O$ (0.2 mL) | —[e] |
| 10 | $K_2CO_3$ | $CH_3CN$ (1.5 mL):$H_2O$ (0.2 mL) | 80 |
| 11 | $K_2CO_3$ | THF (1.5 mL):$H_2O$ (0.2 mL) | 85 |

[a]1:4 ratio of curcumin 20 to nitroalkene 21 was used.
[b]All the reactions were carried out with 1 equiv of base.
[c]2 equiv of base was used.
[d]Isolated yield after silica gel column chromatography.
[e]The reaction was incomplete.
[f]Polymerization.

The reaction is screened with different bases in various solvents. The product is obtained in moderate yields when acetonitrile and THF as solvents with bases such as DBU, $K_2CO_3$, or $KOBu^t$ (Table 1, entries 2-4). When chlorinated solvents are used (Table 1, entries 6 and 7) the reaction is found to be incomplete. To increase the yield, 2 equiv of base was employed, which resulted in polymerization (Table 1, entry 5). Without being bound by any theory, it is believed that the low observed yields are due to insolubility of the base in the reaction media. Small amounts of water were added to the reaction, improving the yields dramatically. Acetonitrile-water and THF-water systems are solvent systems shown to work well for this particular reaction. See (Table 1, entries 10 and 11).

Example 3

Diastereoselectivity. The double Michael addition product 22, is a highly functionalized cyclohexanone containing four contiguous chiral centers. Eight diastereomers are therefore possible and achieving excellent diastereo and enantioselectivity is desired. Initially, a diastereoselective domino double Michael addition was carried out, and the results shown in Table 2. The reaction was incomplete when performed with chlorinated solvents (Table 2, entries 1 and 2). Acetonitrile-water systems provided good yields, although, varying in the amount of water had little to no effect on the diastereoselectivity of the reaction (Table 2, entries 3 and 4). However, for this particular reaction, THF-water proved to provide diastereoselectivity (Table 2, entry 5).

TABLE 2

Diastereoselective double Michael addition of curcumin 20 to nitroalkene 21 in the presence of $K_2CO_3$ in various solvents at room temperature.[a]

| Entry | Solvent | Yield (%)[b] | dr[d] |
|---|---|---|---|
| 1 | $CH_2Cl_2$ (1.5 mL): $H_2O$ (0.2 mL) | —[c] | — |
| 2 | $CHCl_3$ (1.5 mL): $H_2O$ (0.2 mL) | —[c] | — |
| 3 | $CH_3CN$ (1.6 mL): $H_2O$ (0.1 mL) | 70 | 34:66 |
| 4 | $CH_3CN$ (1.5 mL): $H_2O$ (0.1 mL) | 80 | 29:71 |
| 5 | THF (1.5 mL): $H_2O$ (0.2 mL) | 85 | >99:1 |

[a]1:4 ratio of curcumin 20 to nitroalkene 21 was used.
[b]Isolated yield after silica gel column chromatography.
[c]The reaction was incomplete.
[d]Determined by $^1H$ NMR of the crude sample.

Scheme 6

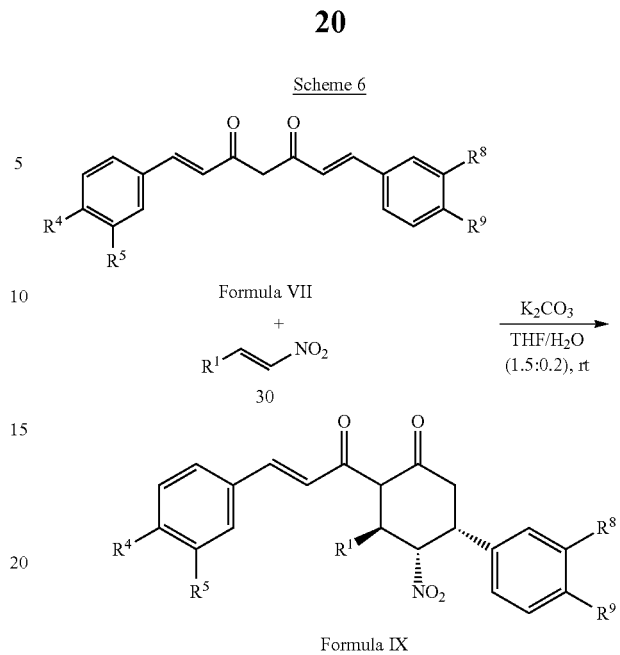

TABLE 3

Diastereoselective preparation of compounds of Formula IX.

| Compound | $R^1$ | $R^4$ | $R^5$ | $R^8$ | $R^9$ | Time (h) | Yield[a] (%) | dr[b] |
|---|---|---|---|---|---|---|---|---|
| IX-1 | 4-OMe—Ph | OMe | H | H | OMe | 3 | 85 | >99:1 |
| IX-2 | 3,4-(OMe)$_2$—Ph | OMe | H | H | OMe | 4 | 86 | >99:1 |
| IX-3 | Ph | OMe | H | H | OMe | 5 | 75 | >99:1 |
| IX-4 | 4-Cl—Ph | OMe | H | H | OMe | 4 | 93 | >99:1 |
| IX-5 | 2-Thienyl | OMe | H | H | OMe | 3 | 88 | >99:1 |
| IX-6 | benzo[d][1,3]dioxole | OMe | H | H | OMe | 4 | 80 | >99:1 |
| IX-7 | 2-Furyl | OMe | H | H | OMe | 3 | 85 | >99:1 |
| IX-8 | 3-NO$_2$—Ph | OMe | H | H | OMe | 2 | 75 | >99:1 |
| IX-9 | PhCH=CH | OMe | H | H | OMe | 2 | 80 | >99:1 |
| IX-10 | 4-OMe—Ph | OMe | OMe | OMe | OMe | 2 | 96 | >99:1 |
| IX-11 | 4-OMe—Ph | OH | OMe | OMe | OH | 2 | 70 | >99:1 |
| IX-12 | 4-OMe—Ph | H | H | H | H | 5 | 67 | >99:1 |
| IX-13 | 2-NO$_2$—Ph | OMe | H | H | OMe | 3 | 80 | >99:1 |
| IX-14 | Cyclohexyl | OMe | H | H | OMe | 2 | 90 | >99:1 |
| IX-15 | n-Butyl | OMe | H | H | OMe | 1 | 99 | >99:1 |
| IX-16 | 4-OMe—Ph | OCH$_2$Ph | OMe | OMe | OCH$_2$Ph | 6 | 93 | >99:1 |

[a]Isolated yield after silica gel column chromatography.
[b]Determined by $^1H$ NMR of the crude sample.

Diastereoselective double Michael addition of Formula VI. Scheme 6 outlines the synthetic procedure for the diastereoselective production compounds of Formula IX, from those of Formula VII, by reaction with various nitroalkenes, as set forth in Table 3. The reaction proceeded smoothly to provide products of Formula VIII in good yields and excellent diastereoselectivity, regardless of the substituents attached to the aromatic ring.

To a solution of the compound of Formula VI (0.12 mmol, 1.0 equiv) and $K_2CO_3$ (0.12 mmol, 1.0 equiv) in THF (1.5 mL) and $H_2O$ (0.2 mL), nitroalkene 30 was added (0.5 mmol, 4.0 equiv), in portions, at room temperature. The resulting reaction mixture was stirred until the reaction was determined to be complete by monitoring the disappearance of compound of Formula VI by thin layer chromatography. The crude product was purified by silicagel column chromatography, eluting with ethyl acetate/petroleum ether (10-40%).

Characterization Data 3,5-Bis(4-Methoxyphenyl)-2-((E)-3-(4-Methoxyphenyl)acryloyl)-4-Nitrocyclohexanone (IX-1)

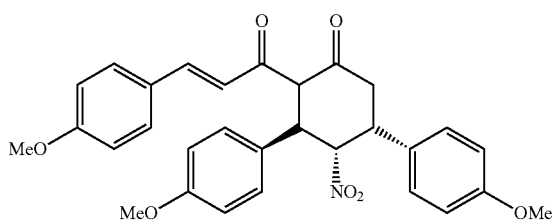

Yellow crystalline solid; Yield 55 mg (85%); mp 200-202° C.; IR (KBr, cm$^{-1}$) 2841 (w), 1787 (w), 1687 (m), 1603 (s), 1578 (s), 1515 (m), 1427 (m), 1260 (s), 1168 (m); NMR (400 MHz, CDCl$_3$) δ 2.84 (dd, J=18.3, 6.1 Hz, 1H), 3.33 (dd, J=18.3, 12.2 Hz, 1H), 3.40-3.44 (m, 1H), 3.76 (s, 3H), 3.81 (s, 3H), 3.82 (s, 3H), 4.68 (d, J=2.1 Hz, 1H), 4.96 (t, J=2.6 Hz, 1H), 6.40 (d, J=5.3 Hz, 1H), 6.82 (dd, J=8.8, 6.7 Hz, 3H), 6.96 (t, J=8.2 Hz, 3H), 7.28-7.31 (m, 6H), 7.66 (d, J=15.3 Hz, 1H), 17.43 (s, 1H); $^{13}$C NMR (100 MHz, CDCl$_3$) δ 33.4, 35.5, 44.5, 55.4 (×2), 55.5, 92.4, 104.5, 114.4, 114.5, 115.0, 117.4, 127.6, 128.4, 129.4, 129.6, 130.2, 133.5, 143.3, 159.3, 159.4, 161.8, 185.6, 187.8.

3-(3,4-Dimethoxyphenyl)-5-(4-Methoxyphenyl)-2-((E)-3-(4-Methoxyphenyl)acryloyl)-4-Nitrocyclohexanone (IX-2)

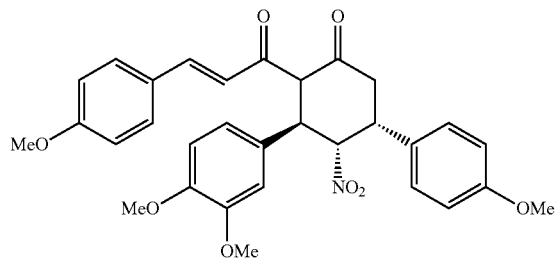

IX-2

Yellow solid; Yield 59 mg (86%); mp 126-128° C.; IR (KBr, cm$^{-1}$) 2926 (w), 2834 (w), 1600 (s), 1512 (m), 1354 (m), 1257 (m), 1172 (w); NMR (400 MHz, CDCl$_3$) δ 2.84 (dd, J=18.4, 6.3 Hz, 1H), 3.33 (q, J=18.5, 12.1 Hz, 1H), 3.42-3.47 (m, 1H), 3.77 (s, 3H), 3.81 (s, 3H), 3.89 (s, 3H), 3.93 (s, 3H), 4.66 (d, J=2.1 Hz, 1H), 5.00 (t, J=2.4 Hz, 1H), 6.42 (d, J=15.3 Hz, 1H), 6.82 (dd, J=8.7, 2.1 Hz, 2H), 6.89 (s, 5H), 6.98 (d, J=8.9 Hz, 1H), 7.26 (d, J=8.8 Hz, 3H), 7.67 (d, J=15.6 Hz, 1H), 17.45 (s, 1H); $^{13}$C NMR (100 MHz, CDCl$_3$) δ 33.2, 35.7, 44.8, 55.3, 55.4, 55.9, 56.2, 92.4, 104.3, 110.7, 111.7, 114.3, 114.4, 117.3, 120.7, 127.5, 128.3, 129.5, 130.2, 133.9, 143.3, 148.8, 149.7, 159.2, 161.7, 185.7, 187.6.

5-(4-Methoxyphenyl)-2-((E)-3-(4-Methoxyphenyl)acryloyl)-4-Nitro-3-Phenylcyclohexanone (IX-3)

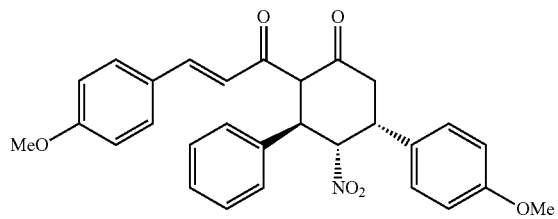

IX-3

Yellow solid; Yield 45 mg (75%); mp 164-165° C.; IR (KBr, cm$^{-1}$) 2930 (w), 1629 (m), 1547 (s), 1510 (m), 1253 (m), 1177 (m), 1032 (m); $^1$H NMR (400 MHz, CDCl$_3$) δ 2.86 (dd, J=19.4, 6.1 Hz, 1H), 3.33 (dd, J=18.4, 12.0 Hz, 1H), 3.41-3.47 (m, 1H), 3.76 (s, 3H), 3.80 (s, 3H), 4.74 (d, J=2.2 Hz, 1H), 5.01 (t, J=2.5 Hz, 1H), 6.37 (d, J=15.3 Hz, 1H), 6.81 (dd, J=18.3, 2.5 Hz, 4H), 6.96 (d, J=9.6 Hz, 2H), 7.24 (d, J=8.8 Hz, 2H), 7.32-7.41 (m, 5H), 7.66 (d, J=15.6 Hz, 1H), 17.45 (s, 1H); $^{13}$C NMR (100 MHz, CDCl$_3$) δ 33.5, 33.6, 45.2, 55.4, 55.5, 92.3, 104.3, 114.4, 114.5, 117.4, 127.6, 128.3 (×2), 128.4, 129.5, 129.7, 130.2, 141.7, 143.3, 159.3, 161.8, 185.4, 188.0.

3-(4-Chlorophenyl)-5-(4-Methoxyphenyl)-2-((E)-3-(4-Methoxyphenyl)acryloyl)-4-Nitrocyclohexanone (IX-4)

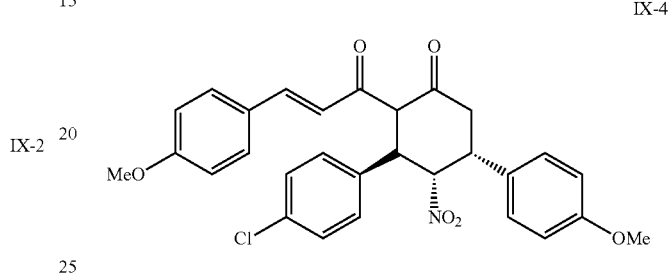

IX-4

Light yellow solid; Yield 59 mg (93%); mp 156-158; IR (KBr, cm$^{-1}$) 2956 (m), 2925 (m), 2853 (m), 1626 (w), 1601 (m), 1548 (s), 1513 (s), 1257 (s), 1172 (s), 829 (s), 738 (s); $^1$H NMR (400 MHz, CDCl$_3$) δ 2.85 (dd, J=16.2, 3.5 Hz, 1H), 3.29-3.41 (m, 2H), 3.77 (s, 3H), 3.81 (s, 3H), 4.72 (d, J=2.1 Hz, 1H), 4.96 (d, J=2.4 Hz, 1H), 6.32 (d, J=15.3 Hz, 1H), 6.83 (t, J=8.3 Hz, 4H), 6.96 (d, J=8.6 Hz, 2H), 7.26 (d, J=8.6 Hz, 2H), 7.38 (dd, J=16.2, 8.5 Hz, 4H), 7.68 (d, J=16.2 Hz, 1H), 17.47 (s, 1H); $^{13}$C NMR (100 MHz, CDCl$_3$) δ 33.5, 33.7, 44.6, 55.4, 55.5, 92.0, 103.8, 114.4, 114.5, 116.9, 127.4, 128.4, 129.2, 129.6, 129.9, 130.5, 134.3, 140.2, 143.8, 159.4, 161.9, 185.4, 188.0.

5-(4-Methoxyphenyl)-2-((E)-3-(4-Methoxyphenyl)acryloyl)-4-Nitro-3-(Thiophen-2-yl)cyclohexanone (IX-5)

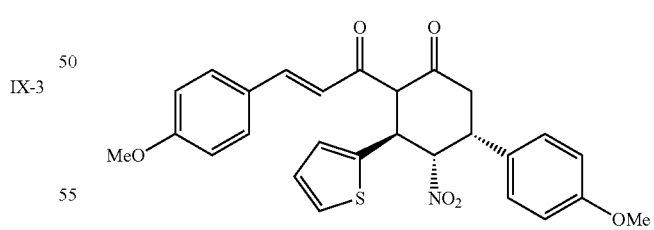

IX-5

Brown solid; Yield 54 mg (88%); mp 160-162° C.; IR (KBr, cm$^{-1}$) 2928 (w), 2833 (w), 1600 (s), 1544 (m), 1512 (m), 1362 (m), 1254 (m), 1173 (m); $^1$H NMR (400 MHz, CDCl$_3$) δ 2.83 (dd, J=9.0, 6.6 Hz, 1H), 3.30 (dd, J=18.9, 12.2 Hz, 1H), 3.55-3.60 (m, 1H), 3.77 (s, 3H), 3.81 (s, 3H), 4.97 (d, J=2.1 Hz, 1H), 5.13 (t, J=2.6 Hz, 1H), 6.54 (d, J=15.3 Hz, 1H), 6.83-6.86 (m, 4H), 7.01-7.06 (m, 4H), 7.31 (dd, J=5.9, 1.5 Hz, 1H), 7.34 (d, J=8.9 Hz, 2H), 7.73 (d, J=15.3 Hz, 1H), 17.42 (s, 1H); $^{13}$C NMR (100 MHz, CDCl$_3$) δ 33.4, 36.1, 40.4, 55.4, 55.5, 92.0, 105.3, 114.4, 114.5, 116.8, 126.3, 126.8, 127.6, 128.4, 128.0, 129.4, 130.4, 143.6, 146.1, 159.3, 161.8, 185.2, 188.2.

3-(Benzo[a][1,3]dioxol-5-yl)-5-(4-Methoxyphenyl)-2-((E)-3-(4-Methoxyphenyl)acryloyl)-4-Nitrocyclohexanone (IX-6)

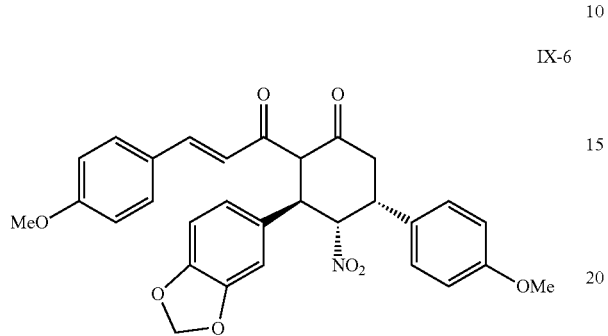

Yellow solid; Yield 54 mg (80%); mp 154-156° C.; IR (KBr, cm$^{-1}$) 2932 (w), 2833 (w), 2717 (w), 1599 (s), 1543 (m), 1512 (m), 1354 (m), 1253 (m), 1171 (m), 1036 (m); $^1$H NMR (400 MHz, CDCl$_3$) δ 2.84 (dd, J=18.6, 6.4 Hz, 1H), 3.32 (dd, J=18.6, 12.2 Hz, 1H), 3.41-3.44 (m, 1H), 3.77 (s, 3H), 3.81 (s, 3H), 4.64 (d, J=2.1 Hz, 1H), 4.97 (t, J=2.6 Hz, 1H), 6.00 (dd, J=5.6, 1.3 Hz, 1H), 6.42 (d, J=15.2 Hz, 1H), 6.81-6.86 (m, 7H), 6.99 (d, J=8.8 Hz, 2H), 7.30 (d, J=8.8 Hz, 3H), 7.68 (d, J=15.2 Hz, 1H), 17.44 (s, 1H); $^{13}$C NMR (100 MHz, CDCl$_3$) δ 33.3, 35.6, 44.9, 55.3, 55.5, 92.3, 101.7, 104.4, 108.3, 109.1, 114.4, 114.5, 117.2, 121.8, 127.5, 128, 129.5, 130.3, 135.5, 143.4, 147.6, 148.7, 159.2, 161.8, 185.7, 187.7.

3-(Furan-2-yl)-5-(4-Methoxyphenyl)-2-((E)-3-(4-Methoxyphenyl)acryloyl)-4-Nitrocyclohexanone (IX-7)

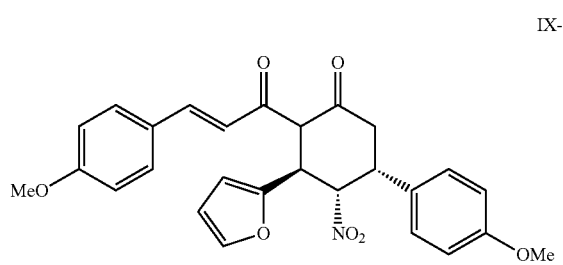

Yellow solid; Yield 54 mg (85%); mp 192° C.; IR (KBr, cm$^{-1}$) 3430 (b), 2930 (m), 2853 (m), 1601 (w), 1552 (m), 1513 (s), 1462 (m), 1367 (w), 1255 (s), 1173 (s), 1030 (m); NMR (400 MHz, CDCl$_3$) δ 2.79 (dd, J=18.6, 6.1 Hz, 1H), 3.29 (dd, J=18.6, 12.5 Hz, 1H), 3.38-3.42 (m, 1H), 3.78 (s, 3H), 3.82 (s, 3H), 4.78 (d, J=2.7 Hz, 1H), 5.31 (t, J=2.7 Hz, 1H), 6.21 (d, J=3.3 Hz, 1H), 6.36 (dd, J=3.3, 1.8 Hz, 1H), 6.48 (d, J=15.8 Hz, 1H), 6.86 (dd, J=8.5, 6.1 Hz, 4H), 7.04 (d, J=8.8 Hz, 2H), 7.39 (d, J=8.5 Hz, 2H), 7.43 (d, J=9.1 Hz, 1H), 7.43 (d, J=9.1 Hz, 1H), 7.75 (d, J=15.2 Hz, 1H), 17.42 (s, 1H); $^{13}$C NMR (100 MHz, CDCl$_3$) δ 33.6, 36.6, 39.4, 55.4, 55.5, 88.2, 102.7, 110.5, 111.1, 114.4, 114.5, 116.4, 127.6, 128.4, 129.5, 130.3, 143.3, 143.5, 153.7, 159.3, 161.8, 184.2, 189.4.

5-(4-Methoxyphenyl)-2-((E)-3-(4-Methoxyphenyl)acryloyl)-4-Nitro-3-(3-nitrophenyl)cyclohexanone (IX-8)

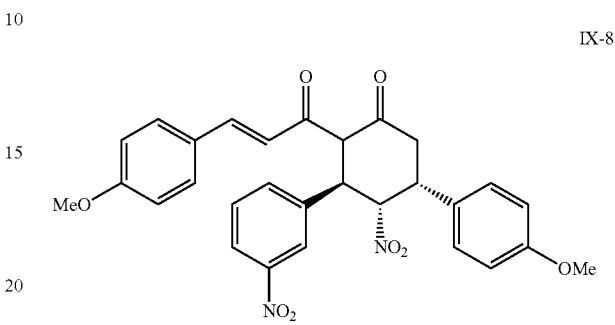

Yellow solid; mp 204-206° C.; IR (KBr, cm$^{-1}$) 2061 (w), 2931 (w), 2839 (w), 1732 (w), 1660 (w), 1601 (s), 1531 (s), 1531 (s), 1513 (s), 1462 (m), 1441 (m), 1410 (m), 1351 (s), 1305 (s), 1255 (s), 1172 (s); $^1$H NMR (400 MHz, CDCl$_3$) δ 2.96 (dd, J=18.0, 6.1 Hz, 1H), 3.33 (dd, J=18.0, 11.3 Hz, 1H), 3.39 (m, 1H), 3.77 (s, 3H), 3.80 (s, 3H), 4.87 (d, J=2.1 Hz, 1H), 5.01 (t, J=2.1 Hz, 1H), 6.27 (d, J=15.2 Hz, 1H), 6.82 (d, J=8.2 Hz, 2H), 6.96 (d, J=8.2 Hz, 2H), 7.24 (d, J=8.7 Hz, 2H), 7.65 (d, J=7.9 Hz, 2H), 7.77 (d, J=7.3 Hz, 1H), 8.20 (d, J=7.9 Hz, 1H), 8.29 (s, 1H) 17.50 (s, 1H); $^{13}$C NMR (100 MHz, CDCl$_3$) δ 33.8, 36.2, 44.4, 55.4, 55.5, 91.6, 103.4, 114.5, 114.6, 116.5, 123.2, 123.5, 127.1, 128.4, 128.7, 130.8, 134.4, 144.1, 144.4, 149.1, 159.5, 162.1, 185.3, 187.9.

5-(4-Methoxyphenyl)-2-((E)-3-(4-Methoxyphenyl)acryloyl)-4-nitro-3-styrylcyclohexanone (IX-9)

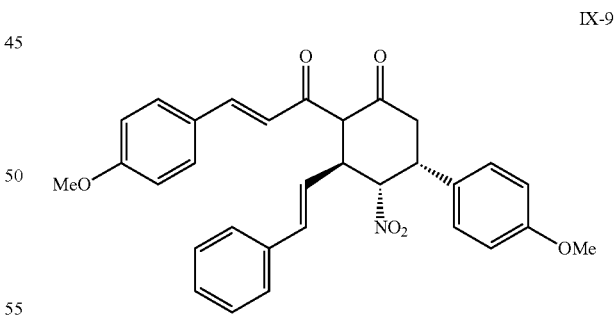

Yellow solid; Yield 51 mg (80%); mp 88-90° C.; IR (KBr, cm$^{-1}$) 2930 (w), 1629 (m), 1547 (s), 1510 (m), 1253 (m), 1177 (m), 1032 (m); $^1$H NMR (400 MHz, CDCl$_3$) δ 2.81 (dd, J=18.9, 6.7 Hz, 1H), 3.32 (dd, J=18.9, 11.9 Hz, 1H), 3.54-3.58 (m, 1H), 3.77 (s, 3H), 3.78 (s, 3H), 4.31 (d, J=5.5 Hz, 1H), 5.01 (unresolved triplet, 1H), 6.42 (dd, J=15.8, 5.5 Hz, 1H), 6.63 (dd, J=26.2, 15.5 Hz, 2H), 6.86 (d, J=8.5 Hz, 4H), 7.11 (d, J=8.5 Hz, 2H), 7.28 (d, J=6.7 Hz, 1H), 7.34 (t, J=7.9 Hz, 2H), 7.42 (dd, J=12.2, 8.5 Hz, 4H), 7.78 (d, J=15.2 Hz, 4H), 17.50 (s, 1H); $^{13}$C NMR (100 MHz, CDCl$_3$) δ 34.0, 36.4, 42.3, 55.4, 55.5, 893, 103.5, 114.5 (×2), 116.9, 126.8, 127.7, 128.5, 128.6, 128.9 129.2, 129.7, 130.3, 135.5, 135.9, 143.5, 159.3, 161.8, 184.1, 189.6.

5-(3,4-dimethoxyphenyl)-3-(4-methoxyphenyl)-2-((E)-3-(3,4-dimethoxyphenyl)acryloyl)-4-Nitrocyclohexanone (IX-10)

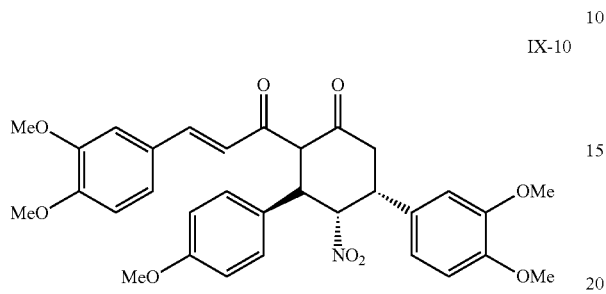

light yellow solid; Yield 68 mg (96%); mp 158-160° C.; IR (KBr, cm$^{-1}$) 3000 (w), 2956 (w), 2935 (w), 2837 (w), 1731 (w), 1624 (w), 1607 (w), 1596 (w), 1547 (m), 1511 (s), 1463 (m), 1421 (m), 1368 (w), 1264 (s), 1141 (s), 1026 (m); NMR (400 MHz, CDCl$_3$) δ 2.88 (dd, J=18.3, 6.1 Hz, 1H), 3.33 (dd, J=18.3, 11.9 Hz, 1H), 3.41-3.73 (m, 1H), 3.811 (s, 3H), 3.814 (3H), 3.83 (3H), 3.84 (s, 3H), 4.68 (d, J=2.1 Hz, 1H), 4.99 (t, J=2.4 Hz, 1H), 6.38 (d, J=15.2 Hz, 1H), 6.54 (d, J=2.1 Hz, 1H), 6.60 (dd, J=8.2, 2.1 Hz, 2H), 6.73 (d, J=1.8 Hz, 1H), 6.78 (dd, J=11.9, 8.2 Hz, 2H), 6.94 (d, J=8.5 Hz, 3H), 7.32 (d, J=8.5 Hz, 3H), 7.64 (d, J=15.5 Hz, 1H), 17.40 (s, 1H); $^{13}$C NMR (100 MHz, CDCl$_3$) δ 33.6, 36.1, 44.4, 55.4, 55.8, 55.9, 56.0, 92.3, 104.6, 109.7, 110.3, 111.0, 111.3, 114.7, 114.9, 117.8, 119.6, 123.2, 127.8, 129.3, 130.4, 133.6, 143.3, 148.8, 149.1, 149.2, 151.5, 159.3, 185.4, 187.6.

5-(4-hydroxy-3-methoxyphenyl)-2-((E)-3-(4-hydroxy-3-methoxyphenyl)acryloyl)-3-(4-methoxyphenyl)-4-nitrocyclohexanone (IX-11)

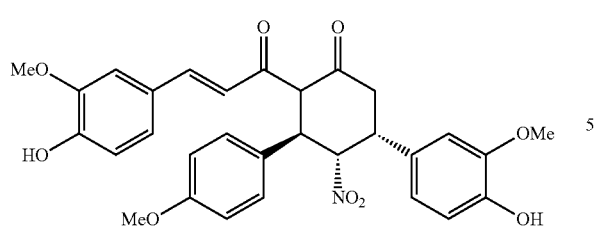

brown crystalline solid; Yield 37 mg (70%); mp 83-85° C.; IR (KBr, cm$^{-1}$) 3455 (s), 3007 (w), 2960 (w), 2938 (w), 2840 (w), 1626 (m), 1603 (s), 1514 (s), 1463 (m), 1428 (m), 1338 (m), 1255 (s), 1173 (m), 1030 (s); $^1$HNMR (400 MHz, CDCl$_3$) δ 2.86 (dd, J=17.7, 5.8 Hz, 1H), 3.31 (dd, J=17.7, 11.9 Hz, 1H), 3.38-3.44 (m, 1H), 3.81 (s, 3H), 3.82 (s, 3H), 3.85 (s, 3H), 4.66 (d, J=2.4 Hz, 1H), 4.98 (t, J=2.4 Hz, 1H), 5.58 (s, 1H), 5.86 (s, 1H), 6.35 (d, J=15.3 Hz, 1H), 6.50-6.56 (m, 2H), 6.72 (d, J=1.6 Hz, 1H), 6.81 (d, J=8.2 Hz, 1H), 6.85 (s, 1H), 6.89 (d, J=2.8 Hz, 1H), 6.94 (d, J=8.8 Hz, 1H), 7.31 (d, J=18.8 Hz, 2H), 7.62 (d, J=15.2 Hz, 1H), 17.38 (s, 1H); $^{13}$C NMR (100 MHz, CDCl$_3$) δ 33.8, 36.2, 44.6, 55.5, 56.0, 56.1, 92.6, 104.6, 109.5, 109.9, 114.8, 115.0, 117.6, 120.6, 123.4, 127.6, 129.4, 129.6, 129.8, 133.7, 143.6, 145.5, 146.8, 146.9, 148.4, 159.5, 185.5, 187.6.

3-(4-methoxyphenyl)-4-nitro-5-phenyl-2-((E)-3-phenylacryloyl)cyclohexanone (IX-12)

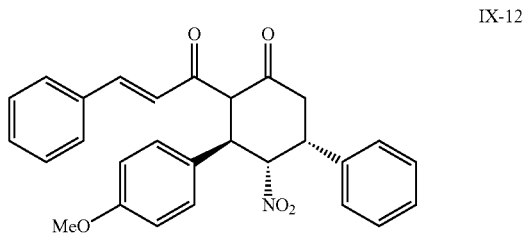 [SMILES: COc1ccc([C@H]2C(C(=O)/C=C/c3ccccc3)C(=O)C[C@H](c3ccccc3)[C@@H]2[N+](=O)[O-])cc1]

Yellow crystalline solid; Yield 38 mg (68%); mp 108-110° C.; IR (KBr, cm$^{-1}$) 3061 (w), 3030 (w), 2930 (w), 2837 (w), 1629 (m), 1609 (m), 1547 (s), 1510 (s), 1451 (m), 1366 (m), 1253 (s), 1177 (m), 1032 (m); $^1$H NMR (400 MHz, CDCl$_3$) δ 2.88 (dd, J=18.3, 6.4 Hz, 1H), 3.40 (dd, J=18.3, 13.5 Hz, 1H), 3.47-3.49 (m, 1H), 3.82 (s), 4.73 (d, J=2.1 Hz, 1H), 5.03 (t, J=2.4 Hz, 1H), 6.55 (d, J=15.5 Hz, 1H), 6.96 (dd, J=8.8, 2.1 Hz, 3H), 7.06 (d, J=5.8 Hz, 2H), 7.27-7.33 (m, 6H), 6.52 (t, J=9.1 Hz, 2H), 7.70 (d, J=15.5 Hz, 1H), 7.98 (d, J=13.4 Hz, 1H), 17.35 (s, 1H); $^{13}$C NMR (100 MHz, CDCl$_3$) δ 33.1, 36.0, 44.5, 55.4, 92.1, 104.8, 115.0, 119.7, 127.2, 128.0, 128.4, 128.9, 129.0, 129.3, 130.5, 133.2, 134.7, 137.6, 143.3, 159.4, 184.9, 188.5.

5-(4-Methoxyphenyl)-2-((E)-3-(4-Methoxyphenyl)acryloyl)-4-Nitro-3-(3-nitrophenyl)cyclohexanone (IX-13)

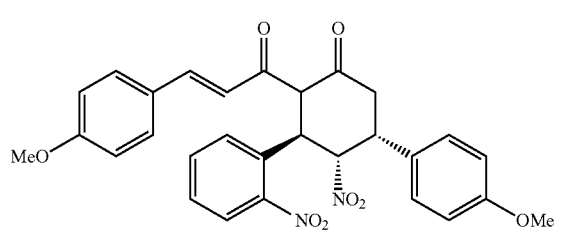

Yellow solid; Yield 49 mg (75%); mp 204-206° C.; IR (KBr, cm$^{-1}$) 3016 (w), 2933 (w), 2838 (w), 1660 (m), 1550 (s), 1513 (s), 1349 (m), 1441 (m), 1410 (m), 1351 (s), 1305 (s), 1255 (s), 1172 (s), 1031 (m); $^1$H NMR (400 MHz, CDCl$_3$) δ 2.89 (dd, J=18.6, 6.8 Hz, 1H), 3.26 (dd, J=18.6, 12.4 Hz, 1H), 3.50-3.53 (m, 1H), 3.77 (s, 3H), 3.81 (s, 3H), 5.07 (unresolved doublet, 1H), 5.27 (unresolved triplet, 1H), 6.30 (d, J=15.0 Hz, 1H), 6.84 (dd, J=8.7, 6.5 Hz, 4H), 6.96 (d, J=8.7 Hz, 2H), 7.29 (s, 2H), 7.52 (t, J=8.6 Hz, 2H), 7.61-7.68 (m, 2H), 7.99 (d, J=8.4 Hz, 1H), 17.43 (s, 1H); $^{13}$C NMR (100 MHz, CDCl$_3$) δ 33.2, 36.3, 40.0, 55.4, 55.5, 89.8, 104.3, 114.5, 114.6, 116.3, 125.4, 127.2, 128.3, 128.9, 129.6, 130.4, 131.4, 133.7, 135.7, 144.4, 149.2, 159.5, 162.1, 185.4, 187.7.

3-cyclohexyl-5-(4-methoxyphenyl)-2-((E)-3-(4-methoxyphenyl)acryloyl)-4-nitrocyclohexanone (IX-14)

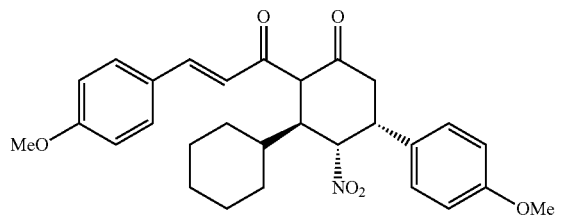

Yellow solid; Yield 58 mg (90%); mp 203-205° C.; IR (KBr, cm$^{-1}$) 2932 (s), 2846 (m), 1624 (m), 1603 (m), 1547 (m), 1508 (w), 1418 (w), 1399 (w), 1247 (s), 1173 (s), 1032 (s); $^1$H NMR (400 MHz, CDCl$_3$) δ 1.05-1.97 (m, 11H), 2.83 (dd, J=18.9, 7.9 Hz, 1H), 3.25 (dd, J=7.9, 2.4 Hz, 1H), 3.37 (dd, J=18.9, 11.3 Hz, 1H), 3.55-3.60 (m, 1H), 3.79 (s, 3H), 3.85 (s, 3H), 5.13 (t, J=2.7 Hz, 1H), 6.65 (d, J=15.2 Hz, 1H), 6.91 (dd, J=18.0, 8.8 Hz, 3H), 7.19 (d, J=8.5 Hz, 3H), 7.50 (d, J=9.5 Hz, 2H), 7.73 (d, J=15.2 Hz, 1H), 17.02 (s, 1H); $^{13}$C NMR (100 MHz, CDCl$_3$) δ 26.3, 26.7, 30.8, 31.9, 34.9, 36.5, 44.7, 44.9, 55.4, 55.6, 87.6, 105.9, 114.5, 114.6, 116.8, 128.0, 128.5, 130.1, 142.1, 159.3, 161.7, 180.2, 192.5.

3-butyl-5-(4-methoxyphenyl)-2-((E)-3-(4-methoxyphenyl)acryloyl)-4-nitrocyclohexanone (IX-15)

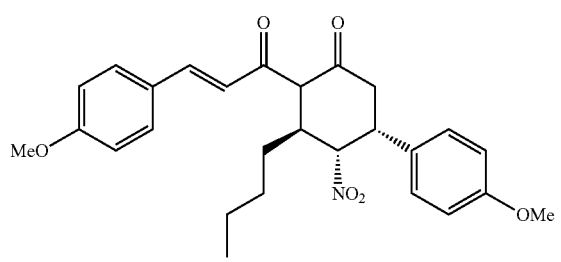

Yellow solid; Yield 58 mg (100%); mp 127-129° C.; IR (KBr, cm$^{-1}$) 2957 (m), 2932 (m), 2870 (m), 1626 (m), 1602 (s), 1547 (s), 1513 (s), 1462 (m), 1368 (w), 1255 (s), 1173 (s), 1032 (m); $^1$H NMR (400 MHz, CDCl$_3$) δ 0.97 (t, J=7.0 Hz, 3H), 1.41-1.76 (m, 6H), 2.75 (dd, J=18.9, 7.0 Hz, 1H), 3.31 (s, 3H), 3.35 (dd, J=12.2, 7.0 Hz, 1H), 3.54 (m, 1H), 3.80 (s, 3H), 3.85 (s, 3H), 4.99 (s, 1H), 6.68 (d, J=15.2 Hz, 1H), 6.91 (dd, J=13.7, 8.5 Hz, 4H), 7.16 (d, J=8.5 Hz, 2H), 7.50 (d, J=8.5 Hz, 2H), 7.78 (d, J=15.2 Hz, 1H), 17.22 (s, 1H); $^{13}$C NMR (100 MHz, CDCl$_3$) δ 14.1, 22.5, 29.7, 34.1, 36.0, 37.3, 39.5, 55.4, 55.5, 88.3, 107.5, 114.5, 114.6, 116.1, 127.8, 128.4, 129.8, 130.1, 142.9, 159.3, 161.7, 181.8, 190.3.

2-((E)-3-(4-(benzyloxy)-3-methoxyphenyl)acryloyl)-5-(4-(benzyloxy)phenyl)-3-(4-methoxyphenyl)-4-nitrocyclohexanone (IX-16)

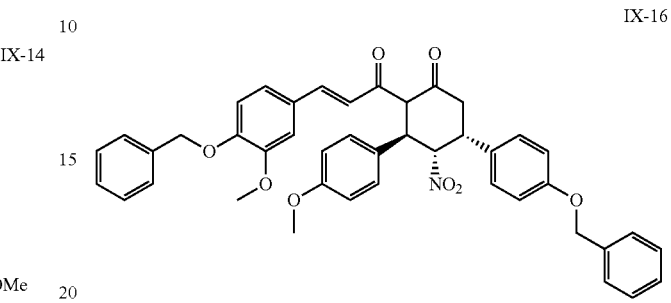

Yellow solid; Yield 90 mg (92%); mp 76-78° C.; IR (KBr, cm$^{-1}$) 3437 (br), 2929 (m), 2857 (w), 1624 (w), 1546 (m), 1510 (s), 1463 (m), 1421 (w), 1371 (w), 1262 (s), 1174 (w), 1140 (m), 1032 (m); $^1$H NMR (400 MHz, CDCl$_3$) δ 2.85 (dd, J=18.3, 6.1 Hz, 1H), 3.31 (dd, J=18.0, 11.9 Hz, 1H), 3.38-3.40 (m, 1H), 3.80 (s, 3H), 3.81 (s, 3H), 3.83 (s, 3H), 4.66 (d, J=1.8 Hz, 1H), 4.97 (t, J=2.4 Hz, 1H), 5.10 (s, 2H), 5.16 (s, 2H), 6.36 (d, J=15.2 Hz, 1H), 6.51 (m, 1H), 6.57 (d, J=1.5 Hz, 2H), 6.74 (d, J=4.8 Hz, 1H), 6.79 (d, J=8.5 Hz, 2H), 6.87-6.94 (m, 4H), 7.28-7.43 (m, 11H), 7.61 (d, J=15.5 Hz, 1H), 17.39 (s, 1H); $^{13}$C NMR (100 MHz, CDCl$_3$) δ 33.7, 36.0, 44.6, 55.4, 55.9, 56.2, 70.9, 71.1, 92.3, 104.6, 110.6, 111.1, 113.4, 114.2, 114.9, 118.0, 119.7, 122.9, 127.3 (×2), 128.0, 128.1, 128.6, 128.7, 129.3, 130.6, 133.6, 136.5, 137.0, 143.3, 148.0, 149.7, 149.9, 150.6, 159.4, 185.4, 187.7.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

Other embodiments are set forth in the following claims.

What is claimed is:

1. A compound of Formula VIII:

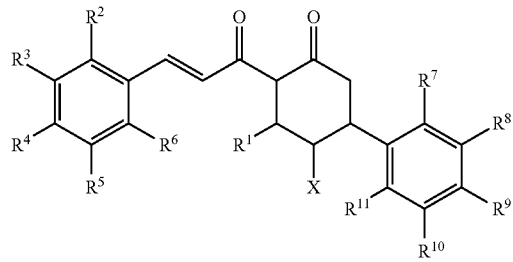

Formula VIII wherein:
X is —C(O)R, —C(O)OR, —CN, —NO$_2$, —S(O)$_2$R', —P(O)(OR)$_2$;
each R is individually H, alkyl, aryl, or alkenyl;
R' is alkyl, aryl, or akenyl;
R$^1$ is aryl, alkenyl, arylalkenyl, heterocyclyl, or heteroaryl; and
R$^2$, R$^3$, R$^4$, R$^5$, R$^6$, R$^7$, R$^8$, R$^9$, R$^{10}$, and R$^{11}$ are individually H, alkoxy, or hydroxy.

2. The compound of claim 1, wherein R$^1$ is phenyl, alkenyl, thiophenyl, or furyl.

3. The compound of claim 1, wherein R$^4$ and R$^9$ are alkoxy.

4. The compound of claim 1, wherein R$^2$, R$^3$, R$^6$, R$^7$, R$^{10}$, and R$^{11}$ are H.

5. The compound of claim 1, wherein X is NO$_2$.

6. The compound of claim 1, wherein Formula VIII is 3,5-bis(4-methoxyphenyl)-2-((e)-3-(4-methoxyphenyl)acryloyl)-4-nitrocyclohexanone; 3-(3,4-dimethoxyphenyl)-5-(4-methoxyphenyl)-2-((E)-3-(4-methoxyphenyl)acryloyl)-4-nitrocyclohexanone; 5-(4-methoxyphenyl)-2-((E)-3-(4-methoxyphenyl)acryloyl)-4-nitro-3-phenylcyclohexanone; 3-(4-chlorophenyl)-5-(4-methoxyphenyl)-2-((E)-3-(4-methoxyphenyl)acryloyl)-4-nitrocyclohexanone; 5-(4-methoxyphenyl)-2-((E)-3-(4-methoxyphenyl)acryloyl)-4-nitro-3-(thiophen-2-yl)cyclohexanone; 3-(benzo[a][1,3]dioxol-5-yl)-5-(4-methoxyphenyl)-2-((E)-3-(4-methoxyphenyl)acryloyl)-4-nitrocyclohexanone; 3-(furan-2-yl)-5-(4-methoxyphenyl)-2-((E)-3-(4-methoxyphenyl)acryloyl)-4-nitrocyclohexanone; 5-(4-methoxyphenyl)-2-((E)-3-(4-methoxyphenyl)acryloyl)-4-nitro-3-(3-nitrophenyl)cyclohexanone; 5-(4-methoxyphenyl)-2-((E)-3-(4-methoxyphenyl)acryloyl)-4-nitro-3-styrylcyclohexanone; 5-(3,4-dimethoxyphenyl)-3-(4-methoxyphenyl)-2-((E)-3-(3,4-dimethoxyphenyl)acryloyl)-4-nitrocyclohexanone; 5-(4-hydroxy-3-methoxyphenyl)-2-((E)-3-(4-hydroxy-3-methoxyphenyl)acryloyl)-3-(4-methoxyphenyl)-4-nitrocyclohexanone; or 3-(4-methoxyphenyl)-4-nitro-5-phenyl-2-((E)-3-phenylacryloyl)cyclohexanone.

7. A method of preparing a compound of Formula VIII comprising:
reacting a compound of Formula VI with a nitroalkene in the presence of a base, wherein:

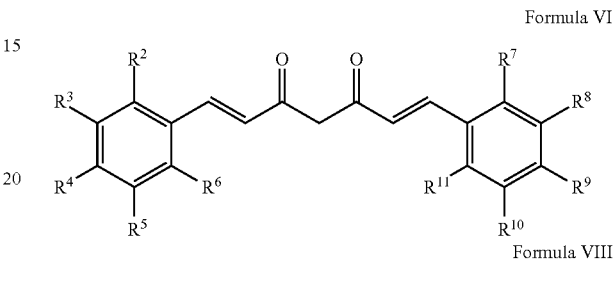

Formula VI

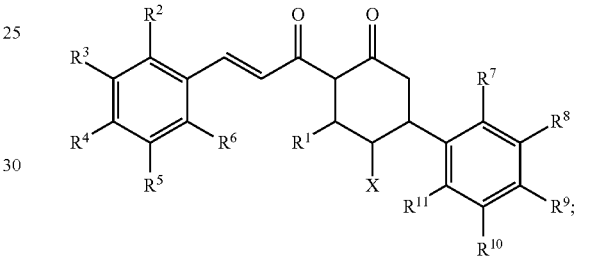

Formula VIII the nitroalkene has formula R$^1$CH=CHNO$_2$;
R$^1$ is aryl, alkene, heterocyclyl, or heteroaryl; and
R$^2$, R$^3$, R$^4$, R$^5$, R$^6$, R$^7$, R$^8$, R$^9$, R$^{10}$, and R$^{11}$ are individually H, alkoxy, or hydroxy.

8. The method of claim 7, wherein the base is a metal alkoxide, metal hydroxide, metal carbonate, metal oxide, metal amide, an amine, a hindered amine, or a mixture of any two or more thereof.

9. The method of claim 7, wherein the compound of Formula VIII, has the stereoselective conformation of the compound of Formula VIII*:

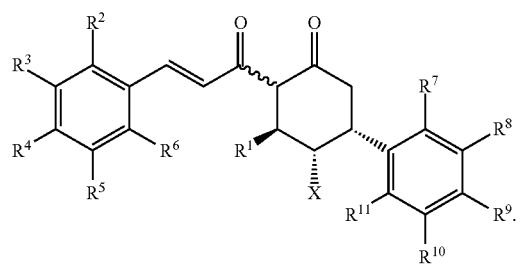

Formula VIII*

10. A pharmaceutical composition comprising the compound of claim 1, and a pharmaceutically acceptable carrier.

* * * * *

UNITED STATES PATENT AND TRADEMARK OFFICE
CERTIFICATE OF CORRECTION

PATENT NO. : 8,410,177 B2
APPLICATION NO. : 12/717774
DATED : April 2, 2013
INVENTOR(S) : Namboothiri et al.

It is certified that error appears in the above-identified patent and that said Letters Patent is hereby corrected as shown below:

On the Title Page, Item (56), under "OTHER PUBLICATIONS", in Column 2, Line 10, delete "anti inflammatory" and insert -- anti-inflammatory --, therefor.

On Title Page 2, Item (56), under "OTHER PUBLICATIONS", in Column 2, Line 24, delete "PCT/IB/2010/001337," and insert -- PCT/IB2010/001337, --, therefor.

In the Specification

In Column 4, Line 30, delete "Sjorgen's" and insert -- Sjögren's --, therefor.

In Column 4, Line 34, delete "dermatitis" and insert -- dermatitis. --, therefor.

In Column 8, Line 36, delete "dimethoxyphenyl)-5-" and insert
-- 3-(3,4-dimethoxyphenyl)-5- --, therefor.

In Column 13, Lines 58-59, delete "manitol," and insert -- mannitol, --, therefor.

In Column 15, Line 21, delete "Sjorgen's" and insert -- Sjögren's --, therefor.

In Column 15, Line 25, delete "dermatitis" and insert -- dermatitis. --, therefor.

In Column 21, Line 3, delete "NMR" and insert -- $^1$H NMR --, therefor.

In Column 21, Line 35, delete "NMR" and insert -- $^1$H NMR --, therefor.

In Column 23, Line 60, delete "NMR" and insert -- $^1$H NMR --, therefor.

In Column 25, Line 1, delete "893" and insert -- 89.7, --, therefor.

Signed and Sealed this
Thirtieth Day of July, 2013

Teresa Stanek Rea
*Acting Director of the United States Patent and Trademark Office*

In Column 25, Line 25, delete "NMR" and insert -- $^1$H NMR --, therefor.

In Column 25, Line 59, delete "$^1$HNMR" and insert -- $^1$H NMR --, therefor.

In the Claims

In Column 29, Line 51, in Claim 6, delete "((e)" and insert -- ((E) --, therefor.